(12) United States Patent
Dong et al.

(10) Patent No.: US 8,003,687 B2
(45) Date of Patent: Aug. 23, 2011

(54) ESTERS OF COMPOUNDS IN THE LEPTOMYCIN FAMILY

(75) Inventors: Steven D. Dong, San Francisco, CA (US); Daniel V. Santi, San Francisco, CA (US)

(73) Assignee: Kosan Biosciences Incorporated, Princeton, NJ (US)

( * ) Notice: Subject to any disclaimer, the term of this patent is extended or adjusted under 35 U.S.C. 154(b) by 630 days.

(21) Appl. No.: 11/991,879

(22) PCT Filed: Sep. 11, 2006

(86) PCT No.: PCT/US2006/035577
§ 371 (c)(1),
(2), (4) Date: Mar. 11, 2008

(87) PCT Pub. No.: WO2007/033214
PCT Pub. Date: Mar. 22, 2007

(65) Prior Publication Data
US 2010/0222382 A1    Sep. 2, 2010

Related U.S. Application Data

(60) Provisional application No. 60/716,453, filed on Sep. 12, 2005.

(51) Int. Cl.
*A01N 43/16*    (2006.01)
*A61K 31/35*    (2006.01)
*C07D 309/38*   (2006.01)

(52) U.S. Cl. ........................ 514/451; 549/294
(58) Field of Classification Search .................. 549/294; 514/451
See application file for complete search history.

(56) References Cited

U.S. PATENT DOCUMENTS

| | | | |
|---|---|---|---|
| 4,771,070 | A | 9/1988 | Hokanson |
| 4,792,522 | A | 12/1988 | Nettleton |
| 5,510,118 | A | 4/1996 | Bosch |
| 5,534,270 | A | 7/1996 | DeCastro |
| 5,662,883 | A | 9/1997 | Bagchi |
| 2003/0162740 | A1 | 8/2003 | Wang |

OTHER PUBLICATIONS

Wang et al., Helvetica Chimica Acta (1997), 80(7), 2157-2167.*
Banker (Modern Pharmaceutics) Banker, G.S. et al, "Modern Pharmaceutics, 3ed.", Marcel Dekker, New York, 1996, pp. 451 and 596.*
Wolff, Manfred E. "Burger's Medicinal Chemistry, 5ed, Part I", John Wiley & Sons, 1995, pp. 975-977.*
West, Anthony R., Solid State Chemistry and its Applications, Wiley, New York, 1988, pp. 358 & 365.*
Meissner, FEBS Letters 576: 27-30 (2004).
Kudo, Experimental Cell Research 242: 540-547 (1998).
Ando, Bioorganic & Medicinal Chemistry Letters 16: 3315-18 (2006).
Kuhnt, Advances in Environmental Microbiolofy 64: 714-20 (1998).
Lecane, Prostate 54:258-267 (2003).
Kudo, Proceedings of the national Academy of Science USA, 96:9112-9117 (1999).
Hietanen, Proceedings of the National Academy of Science USA, 97: 8501-6 (2000).
Vigneri, Nature Medicine, 7: 228-34 (2001).
Vousden, Nature Cancer, 2: 594-604 (2002).
Fukuda, Nature, 390: 308-311 (1997).
Schaumberg, Journal of the Chemical Society, Chemical Communications, 1450-2 (1984).
Nishi, Journal of Biological Chemistry, 269: 6320-4 (1994).
Komiyama, Journal of Antibiotics, 38: 427-9 (1985).
PCT/US2006/035577 International Preliminary Report on Patentability, Mar. 18, 2008.

* cited by examiner

*Primary Examiner* — D Seaman
*Assistant Examiner* — Niloofar Rahmani
(74) *Attorney, Agent, or Firm* — Laurelee A. Duncan

(57) ABSTRACT

Esters of compounds in the leptomycin family, having a structure according to formula I

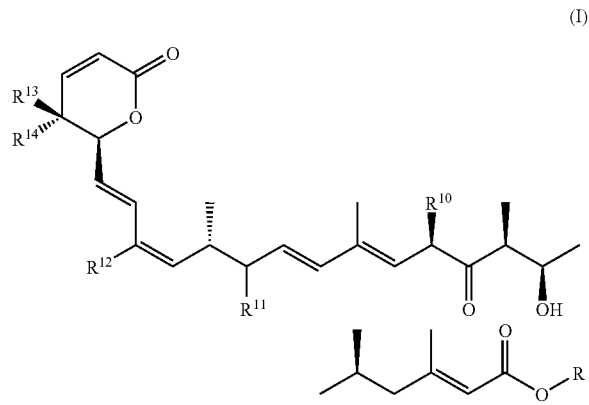

(I)

where R, $R^{10}$, $R^{11}$, $R^{12}$, $R^{13}$, and $R^{14}$ are as defined herein, exhibit anti-tumor properties.

5 Claims, No Drawings

ESTERS OF COMPOUNDS IN THE LEPTOMYCIN FAMILY

This invention was made with US Government support under Grant No. 1 R43 CA109840-01, awarded by National Institutes of Health. The US Government has certain rights in this invention.

TECHNICAL FIELD OF THE INVENTION

This invention relates to esters Of compounds in the leptomycin family and methods for making and using them.

BACKGROUND OF THE INVENTION

Leptomycin B ("LMB") is an anti-tumor, anti-microbial natural product originally isolated from *Steptomyces* spp., as reported in Hokanson et al., U.S. Pat. No. 4,771,070 (1988) and Nettleton et al., U.S. Pat. No. 4,792,522 (1988).

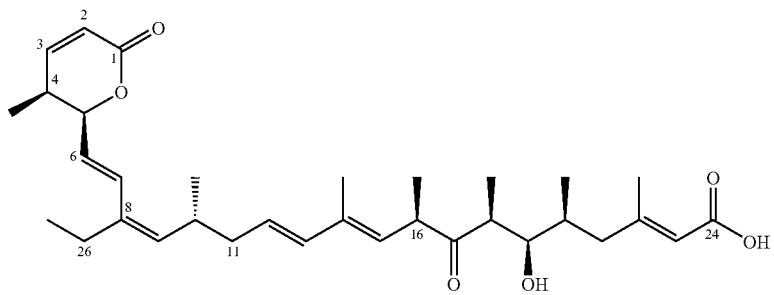

Leptomycin B

LMB is the archetype of a natural product family referred to as the leptomycin family, characterized by a 2,3-dehydro-δ-valerolactone ring at one end of the molecule ($C_1$-$C_5$) and an extended carbon chain having a 6E,8Z and a 12E,14E diene system located off $C_5$. A nitromethyl valerolactone LMB analog has been found to be inactive, whereas biotinylated LMB has been found to be active, suggesting that the 2,3-dehydro-δ-valerolactone structure is a crucial pharmacophore. Kudo et al., *Exp. Cell Res.* 1998, 242, 540-547.

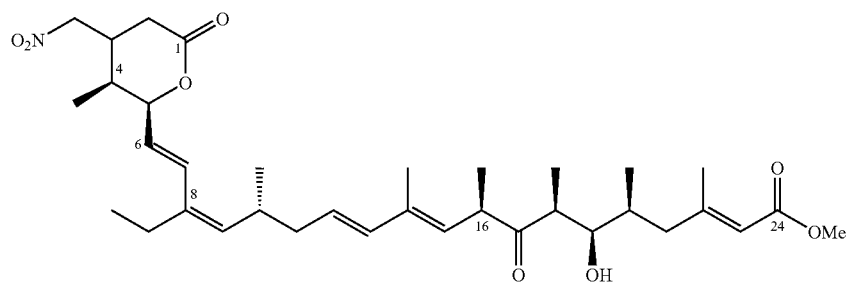

Nitromethyl
valerolactone
leptomycin B
analog

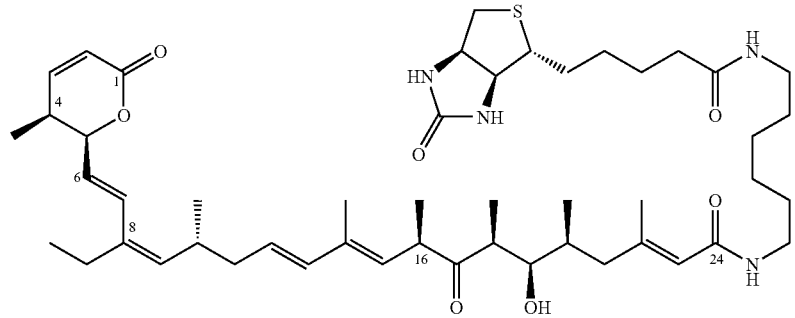

Biotinylated
leptomycin B

Other members of the leptomycin family include leptomycin A, ratjadone, anguinomycins A-D, callystatin A, kazusamycin A (also known as CL-1957B), kazusamycin B (also known as CL-1957E), leptolstatin, and leptofuranins A-D. The formulae of the other family members most structurally similar to leptomycin B are shown:

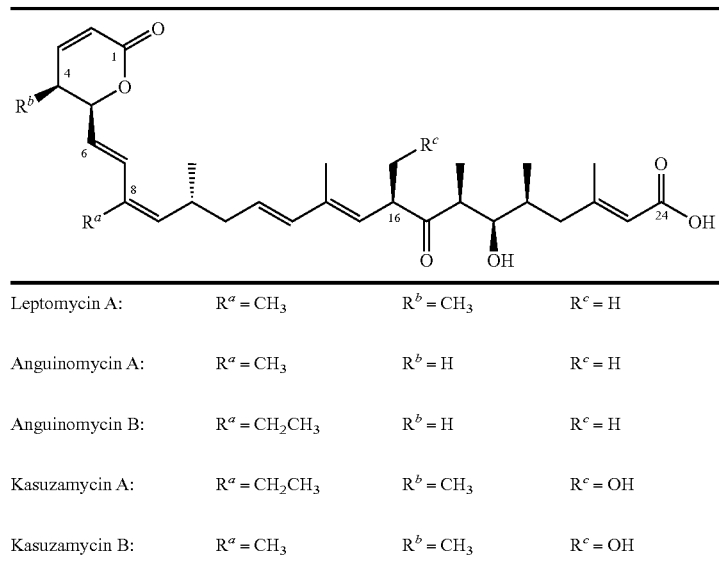

| | | | |
|---|---|---|---|
| Leptomycin A: | $R^a = CH_3$ | $R^b = CH_3$ | $R^c = H$ |
| Anguinomycin A: | $R^a = CH_3$ | $R^b = H$ | $R^c = H$ |
| Anguinomycin B: | $R^a = CH_2CH_3$ | $R^b = H$ | $R^c = H$ |
| Kasuzamycin A: | $R^a = CH_2CH_3$ | $R^b = CH_3$ | $R^c = OH$ |
| Kasuzamycin B: | $R^a = CH_3$ | $R^b = CH_3$ | $R^c = OH$ |

Although originally identified as a result of screening for antimicrobial activity, current interest in LMB resides primarily in its potential as an anti-tumor agent. See, e.g., Komiyama et al., *J. Antibiotics* 1985, 38 (3), 427-429; Wang et al., US 2003/0162740 A1 (2003). At the cellular level, LMB acts by arresting cells at the end of the G1 and G2 phases of the cell cycle. At the molecular level, LMB acts as an inhibitor of the nuclear export receptor CRM1, which binds to and affects the nuclear translocation of "cargo proteins" such as P53, P73, STAT1, (i) ADAR1, Rev, actin, and Bcr-abl. Nishi et al., *J Biol. Chem.* 1994, 269 (9), 6320-6324; Fukuda et al., *Nature* 1997, 390, 308-311; Kudo et al., cited supra.

However, LMB exhibits remarkable cytotoxicity towards mammalian cells (Hamamoto et al., *J. Antibiotics* 1983, 36 (6), 639-645), tempering its attractiveness as an anti-cancer agent. Thus, a phase 1 trial of LMB was halted in 1994 due to extreme toxicity. In an effort to identify more promising anti-cancer agents that exhibit LMB-like activity but are less toxic, LMB was subjected to a bioconversion screening with a number of bacteria and fungi, from which a number of derivatives were isolated (Kuhnt et al., *Applied Environ. Microbiol.* 1998, 64 (2), 714-720): 26-hydroxyleptomycin B, 4,11-dihydroxyleptomycin B, 2,3-dihydroleptomycin B, and leptomycin B glutaminamide.

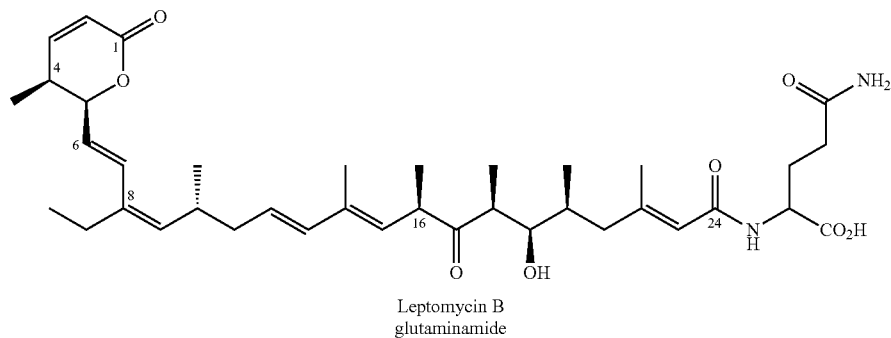

Leptomycin B
glutaminamide

This approach suffers from several drawbacks. The structural diversity in the products obtained was poor: the types of functional groups introduced were limited and the positions into which they were introduced were haphazard, precluding the systematic derivation of a structure-activity relationship. The number of compounds obtained in return for the effort expended was small (four compounds from a screening involving a total of 101 bacterial and fungal strains). The bioconversion yields were often low. Thus, an alternative approach to obtaining leptomycin compounds for use as an anti-cancer agent is desirable.

The prior art is generally devoid of disclosures relating to LMB esters. Kudo et al., *Experimental Cell Research*, 1998, 242, 540-547 (citing Schaumber et al., *J. Chem. Soc. Chem. Commun.*, 1984, 1450-1452) refers to the methyl ester of LMB, not as a biologically active molecule, but instead as an intermediate for the synthesis of another leptomycin compound that was itself inactive.

BRIEF SUMMARY OF THE INVENTION

The present invention provides compounds having a structure according to formula I

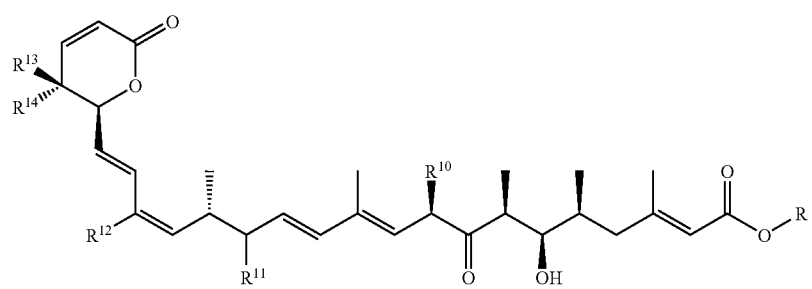

and the pharmaceutically acceptable solvates, hydrates and prodrug forms thereof,
wherein
R is $C_2$-$C_4$ alkyl, $C_2$-$C_4$ alkenyl, $C_2$-$C_4$ alkynyl, cycloaliphatic, aryl, heterocycloaliphatic, heteroaryl, or $(CH_2)_nR^1$;
$R^1$ is aryl, heteroaryl, cycloaliphatic, heterocycloaliphatic, or $C(=O)OR^2$;
$R^2$ is $C_2$-$C_4$ alkyl, cycloaliphatic, heterocycloaliphatic, aryl, or heteroaryl;
n is 1, 2, 3, or 4;
$R^{10}$ is $CH_3$ or $CH_2OH$;
$R^{11}$ is H or OH;
$R^{12}$ is $CH_3$, $CH_2CH_3$, or $CH(OH)CH_3$; and
one of $R^{13}$ and $R^{14}$ is H or $CH_3$ and the other is H or OH.

In a second embodiment, there is provided a method of inhibiting the proliferation of a target cell, comprising contacting the target cell with an effective amount of a compound of this invention. The target cell can be a cancer cell, especially a human breast cancer, lung cancer, ovarian cancer, or leukemia cell. Also, the target cell can be a human papilloma virus (HPV)-associated cervical cancer cell or a bladder cancer cell.

In a third embodiment, there is provided a method of treating a hyperproliferative disease, comprising administering to a patient suffering from such hyperproliferative disease a therapeutically effective amount of a compound of this invention. The hyperproliferative disease so treated may be cancer, especially breast cancer, lung cancer, ovarian cancer, or leukemia. Also, the hyperproliferative disease can be HPV-associated cervical cancer or bladder cancer. The patient preferably is a mammal, especially a human.

In a fourth embodiment, there is provided the use of a compound of this invention for the preparation of a medicament for treating a hyperproliferative disease, which can be cancer, especially breast cancer, lung cancer, ovarian cancer, or leukemia. Also, the cancer can be HPV-associated cervical cancer or bladder cancer.

In a fifth embodiment, there is provided a pharmaceutical formulation comprising a compound of this invention and an excipient.

In a sixth embodiment, there is provided a method of inhibiting the export of a protein from the nucleus of a cell via a CRM1-mediated process, comprising contacting said cell with an inhibitory amount of a compound according to this invention.

In a seventh embodiment, there is provided the use of a compound of this invention for the preparation of a medicament for treating a hyperproliferative disease.

DETAILED DESCRIPTION OF THE INVENTION

Definitions

"Aliphatic" means a straight- or branched-chain, saturated or unsaturated, non-aromatic hydrocarbon moiety having the specified number of carbon atoms (e.g., as in "$C_3$ aliphatic," "$C_1$-$C_5$ aliphatic," or "$C_1$ to $C_5$ aliphatic," the latter two phrases being synonymous for an aliphatic moiety having from 1 to 5 carbon atoms) or, where the number of carbon atoms is not specified, from 1 to 4 carbon atoms (2 to 4 carbons in the instance of unsaturated aliphatic moieties).

"Alkyl" means a saturated aliphatic moiety, with the same convention for designating the number of carbon atoms being applicable. By way of illustration, $C_1$-$C_4$ alkyl moieties include, but are not limited to, methyl, ethyl, propyl, isopropyl, isobutyl, t-butyl, 1-butyl, 2-butyl, and the like.

"Alkenyl" means an aliphatic moiety having at least one carbon-carbon double bond, with the same convention for designating the number of carbon atoms being applicable. By way of illustration, $C_2$-$C_4$ alkenyl moieties include, but are not limited to, ethenyl (vinyl), 2-propenyl(allyl or prop-2-enyl), cis-1-propenyl, trans-1-propenyl, E- (or Z-)2-butenyl, 3-butenyl, 1,3-butadienyl(but-1,3-dienyl) and the like.

"Alkynyl" means an aliphatic moiety having at least one carbon-carbon triple bond, with the same convention for designating the number of carbon atoms being applicable. By way of illustration, $C_2$-$C_a$ alkynyl groups include ethynyl (acetylenyl), propargyl(prop-2-ynyl), 1-propynyl, but-2-ynyl, and the like.

"Cycloaliphatic" means a saturated or unsaturated, non-aromatic hydrocarbon moiety having from 1 to 3 rings and each ring having from 3 to 8 (preferably from 3 to 6) carbon atoms. "Cycloalkyl" means a cycloaliphatic moiety in which each ring is saturated. "Cycloalkenyl" means a cycloaliphatic moiety in which at least one ring has at least one carbon-carbon double bond. "Cycloalkynyl" means a cycloaliphatic moiety in which at least one ring has at least one carbon-carbon triple bond. By way of illustration, cycloaliphatic moieties include, but are not limited to, cyclopropyl, cyclobutyl, cyclopentyl, cyclopentenyl, cyclohexyl, cyclohexenyl, cycloheptyl, cyclooctyl, and adamantyl. Preferred cycloaliphatic moieties are cycloalkyl ones, especially cyclopropyl, cyclobutyl, cyclopentyl, and cyclohexyl.

"Heterocycloaliphatic" means a cycloaliphatic moiety wherein, in at least one ring thereof, up to three (preferably 1 to 2) carbons have been replaced with a heteroatom independently selected from N, O, or S, where the N and S optionally may be oxidized and the N optionally may be quaternized. Similarly, "heterocycloalkyl," "heterocycloalkenyl," and "heterocycloalkynyl" means a cycloalkyl, cycloalkenyl, or cycloalkynyl moiety, respectively, in which at least one ring thereof has been so modified. Exemplary heterocycloaliphatic moieties include aziridinyl, azetidinyl, 1,3-dioxanyl, oxetanyl, tetrahydrofuryl, pyrrolidinyl, piperidinyl, piperazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolanyl, tetrahydro-1,1-dioxothienyl, 1,4-dioxanyl, thietanyl, and the like.

"Alkoxy", "aryloxy", "alkylthio", and "arylthio" mean —O(alkyl), —O(aryl), —S(alkyl), and —S(aryl), respectively. Examples are methoxy, phenoxy, methylthio, and phenylthio, respectively.

"Halogen" or "halo" means fluorine, chlorine, bromine or iodine.

"Aryl" means a hydrocarbon moiety having a mono-, bi-, or tricyclic ring system wherein each ring has from 3 to 7 carbon atoms and at least one ring is aromatic. The rings in the ring system may be fused to each other (as in naphthyl) or bonded to each other (as in biphenyl) and may be fused or bonded to non-aromatic rings (as in indanyl or cyclohexylphenyl). By way of further illustration, aryl moieties include, but are not limited to, phenyl, naphthyl, tetrahydronaphthyl, indanyl, biphenyl, phenanthryl, anthracenyl, and acenaphthyl.

"Heteroaryl" means a moiety having a mono-, bi-, or tricyclic ring system wherein each ring has from 3 to 7 carbon atoms and at least one ring is an aromatic ring containing from 1 to 4 heteroatoms independently selected from N, O, or S, where the N and S optionally may be oxidized and the N optionally may be quaternized. Such at least one heteroatom containing aromatic ring may be fused to other types of rings (as in benzofuranyl or tetrahydroisoquinolyl) or directly bonded to other types of rings (as in phenylpyridyl or 2-cyclopentylpyridyl). By way of further illustration, heteroaryl moieties include pyrrolyl, furanyl, thiophenyl(thienyl), imidazolyl, pyrazolyl, oxazolyl, isoxazolyl, thiazolyl, isothiazolyl, triazolyl, tetrazolyl, pyridyl, N-oxopyridyl, pyridazinyl, pyrimidinyl, pyrazinyl, quinolinyl, isoquinolynyl, quinazolinyl, cinnolinyl, quinozalinyl, naphthyridinyl, benzofuranyl, indolyl, benzothiophenyl, oxadiazolyl, thiadiazolyl, phenothiazolyl, benzimidazolyl, benzotriazolyl, dibenzofuranyl, carbazolyl, dibenzothiophenyl, acridinyl, and the like.

Where it is indicated that a moiety may be substituted, such as by use of "substituted or unsubstituted" or "optionally substituted" phrasing as in "substituted or unsubstituted $C_1$-$C_5$ alkyl" or "optionally substituted heteroaryl," such moiety may have one or more independently selected substituents, preferably one to five in number, more preferably one or two in number. Substituents and substitution patterns can be selected by one of ordinary skill in the art, having regard for the moiety to which the substituent is attached, to provide compounds that are chemically stable and that can be synthesized by techniques known in the art as well as the methods set forth herein.

"Arylalkyl", (heterocycloaliphatic)alkyl", "arylalkenyl", "arylalkynyl", "biarylalkyl", and the like mean an alkyl, alkenyl, or alkynyl moiety, as the case may be, substituted with an aryl, heterocycloaliphatic, biaryl, etc., moiety, as the case may be, with the open (unsatisfied) valence at the alkyl, alkenyl, or alkynyl moiety, for example as in benzyl, phenethyl, N-imidazoylethyl, N-morpholinoethyl, and the like. Conversely, "alkylaryl", "alkenylcycloalkyl", and the like mean an aryl, cycloalkyl, etc., moiety, as the case may be, substituted with an alkyl, alkenyl, etc., moiety, as the case may be, for example as in methylphenyl (tolyl) or allylcyclohexyl. "Hydroxyalkyl", "haloalkyl", "alkylaryl", "cyanoaryl", and the like mean an alkyl, aryl, etc., moiety, as the case may be, substituted with one or more of the identified substituent (hydroxyl, halo, etc., as the case may be).

By way of illustration, permissible substituents include, but are not limited to, alkyl (especially methyl or ethyl), alkenyl (especially allyl), alkynyl, aryl, heteroaryl, cycloaliphatic, heterocycloaliphatic, halo (especially fluoro), haloalkyl (especially trifluoromethyl), hydroxyl, hydroxyalkyl (especially hydroxyethyl), cyano, nitro, alkoxy, —O(hydroxyalkyl), —O (haloalkyl) (especially —OCF$_3$), —O(cycloalkyl), —O(heterocycloalkyl), —O (aryl), alkylthio, arylthio, =O, =NH, =N(alkyl), =NOH, =NO(alkyl), —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(cycloalkyl), —S(=O)alkyl, —SO$_2$(alkyl), —SO$_2$NH$_2$, —SO$_2$NH(alkyl), —SO$_2$N(alkyl)$_2$, and the like.

Where the moiety being substituted is an aliphatic moiety, preferred substituents are aryl, heteroaryl, cycloaliphatic, heterocycloaliphatic, halo, hydroxyl, cyano, nitro, alkoxy, —O (hydroxyalkyl), —O (haloalkyl), —O(cycloalkyl), —O(heterocycloalkyl), —O (aryl), alkylthio, arylthio, =O, =NH, =N(alkyl), =NOH, =NO(alkyl), —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(cycloalkyl), —S(=O)alkyl, —SO$_2$(alkyl), —SO$_2$NH$_2$, —SO$_2$NH(alkyl), and —SO$_2$N(alkyl)$_2$. More preferred substituents are halo, hydroxyl, cyano, nitro, alkoxy, —O(aryl), =O, =NOH, =NO(alkyl), —OC(=O)(alkyl), —OC(=O)O(alkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NHC(=O)

(alkyl), —NHC(=O)H, —NHC(=O)NH$_2$, —NHC(=O)NH(alkyl), —NHC(=O)N(alkyl)$_2$, and —NHC(=NH)NH$_2$.

Where the moiety being substituted is a cycloaliphatic, heterocycloaliphatic, aryl, or heteroaryl moiety, preferred substituents are alkyl, alkenyl, alkynyl, halo, haloalkyl, hydroxyl, hydroxyalkyl, cyano, nitro, alkoxy, —O (hydroxyalkyl), —O (haloalkyl), —O(cycloalkyl), —O(heterocycloalkyl), —O(aryl), alkylthio, arylthio, —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(cycloalkyl), —S(=O)alkyl, —SO$_2$(alkyl), —SO$_2$NH$_2$, —SO$_2$NH(alkyl), and —SO$_2$N(alkyl)$_2$. More preferred substituents are alkyl, alkenyl, halo, haloalkyl, hydroxyl, hydroxyalkyl, cyano, nitro, alkoxy, —O(hydroxyalkyl), —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, —NH$_2$, —NH(alkyl), —N(alkyl)$_2$, —NH(aryl), —NHC(=O)(alkyl), —NHC(=O)H, —NHC(=O)NH$_2$, —NHC(=O)NH(alkyl), —NHC(=O)N(alkyl)$_2$, and —NHC(=NH)NH$_2$.

Where a range is stated, as in "C$_1$ to C$_5$ alkyl" or "5 to 10%," such range includes the end points of the range.

Unless particular stereoisomers are specifically indicated (e.g., by a bolded or dashed bond at a relevant stereocenter in a structural formula, by depiction of a double bond as having E or Z configuration in a structural formula, or by use stereochemistry-designating nomenclature), all stereoisomers are included within the scope of the invention, as pure compounds as well as mixtures thereof. Unless otherwise indicated, individual enantiomers, diastereomers, geometrical isomers, and combinations and mixtures thereof are all encompassed by the present invention.

Those skilled in the art will appreciate that compounds may have tautomeric forms (e.g., keto and enol forms), resonance forms, and zwitterionic forms that are equivalent to those depicted in the structural formulae used herein and that the structural formulae encompass such tautomeric, resonance, or zwitterionic forms.

"Pharmaceutically acceptable salt" means a salt of a compound suitable for pharmaceutical formulation. Where a compound has one or more basic functionalities, the salt can be an acid addition salt, such as a sulfate, hydrobromide, tartrate, mesylate, maleate, citrate, phosphate, acetate, pamoate (embonate), hydroiodide, nitrate, hydrochloride, lactate, methylsulfate, fumarate, benzoate, succinate, mesylate, lactobionate, suberate, tosylate, and the like. Where a compound has one or more acidic moieties, the salt can be a salt such as a calcium salt, potassium salt, magnesium salt, meglumine salt, ammonium salt, zinc salt, piperazine salt, tromethamine salt, lithium salt, choline salt, diethylamine salt, 4-phenylcyclohexylamine salt, benzathine salt, sodium salt, tetramethylammonium salt, and the like. Polymorphic crystalline forms and solvates are also encompassed within the scope of this invention.

Compounds and Methods

In a preferred embodiment, in formula I R$^{10}$ is CH$_3$; R$^{11}$ is H; R$^{12}$ is CH$_2$CH$_3$; R$^{13}$ is CH$_3$, and R$^{14}$ is H—that is, compounds that are esters of leptomycin B. More preferably, R is C$_2$-C$_a$ alkyl, C$_2$-C$_4$ alkenyl, C$_2$-C$_4$ alkynyl, or CH$_2$R$^1$, where R$^1$ is aryl, heteroaryl, cycloaliphatic, heterocycloaliphatic, or C(=O)OR$^2$, where R$^2$ is C$_2$-C$_4$ alkyl.

In another preferred embodiment of the invention, the group R formula I is CH$_2$R$^1$. More preferably, in such instance R$^1$ is aryl, heteroaryl, or C(=O)OR$^2$, where R$^2$ is C$_2$-C$_4$ alkyl.

Compounds of this invention can be used for treating diseases such as, but not limited to, hyperproliferative diseases, including: cancers of the head and neck which include tumors of the head, neck, nasal cavity, paranasal sinuses, nasopharynx, oral cavity, oropharynx, larynx, hypopharynx, salivary glands, and paragangliomas; cancers of the liver and biliary tree, particularly hepatocellular carcinoma; intestinal cancers, particularly colorectal cancer; treat ovarian cancer; small cell and non-small cell lung cancer; breast cancer sarcomas, such as fibrosarcoma, malignant fibrous histiocytoma, embryonal rhabdomysocarcoma, leiomysosarcoma, neurofibrosarcoma, osteosarcoma, synovial sarcoma, liposarcoma, and alveolar soft part sarcoma; neoplasms of the central nervous systems, particularly brain cancer; lymphomas such as Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, and T-cell anaplastic large cell lymphoma. Clinically, practice of the methods and use of compositions described herein will result in a reduction in the size or number of the cancerous growth and/or a reduction in associated symptoms (where applicable). Pathologically, practice of the method and use of compositions described herein will produce a pathologically relevant response, such as: inhibition of cancer cell proliferation, reduction in the size of the cancer or tumor, prevention of further metastasis, and inhibition of tumor angiogenesis. The method of treating such diseases comprises administering a therapeutically effective amount of an inventive combination to a subject. The method may be repeated as necessary. Especially, the cancer can be prostate cancer, human papilloma virus (HPV)-associated cervical cancer, leukemia (especially chronic myeloid leukemia or CML), and bladder cancer.

Non-cancer disorders that are characterized by cellular hyperproliferation can also be treated by compounds of this invention. Illustrative examples of such disorders include but are not limited to: atrophic gastritis, inflammatory hemolytic anemia, graft rejection, inflammatory neutropenia, bullous pemphigoid, coeliac disease, demyelinating neuropathies, dermatomyositis, inflammatory bowel disease (ulcerative colitis and Crohn's disease), multiple sclerosis, myocarditis, myositis, nasal polyps, chronic sinusitis, pemphigus vulgaris, primary glomerulonephritis, psoriasis, surgical adhesions, stenosis or restenosis, scleritis, scleroderma, eczema (including atopic dermatitis, irritant dermatitis, allergic dermatitis), periodontal disease (i.e., periodontitis), polycystic kidney disease, and type I diabetes. Other examples include vasculitis (e.g., Giant cell arteritis (temporal arteritis, Takayasu's arteritis), polyarteritis nodosa, allergic angiitis and granulomatosis (Churg-Strauss disease), polyangitis overlap syndrome, hypersensitivity vasculitis (Henoch-Schonlein purpura), serum sickness, drug-induced vasculitis, infectious vasculitis, neoplastic vasculitis, vasculitis associated with connective tissue disorders, vasculitis associated with congenital deficiencies of the complement system, Wegener's granulomatosis, Kawasaki's disease, vasculitis of the central nervous system, Buerger's disease and systemic sclerosis); gastrointestinal tract diseases (e.g., pancreatitis, Crohn's disease, ulcerative colitis, ulcerative proctitis, primary sclerosing cholangitis, benign strictures of any cause including ideopathic (e.g., strictures of bile ducts, esophagus, duodenum, small bowel or colon); respiratory tract diseases (e.g., asthma, hypersensitivity pneumonitis, asbestosis, silicosis and other forms of pneumoconiosis, chronic bronchitis and chronic obstructive airway disease); nasolacrimal duct diseases (e.g., strictures of all causes including ideopathic); and eustachean tube diseases (e.g., strictures of all causes including ideopathic). Especially, the non-cancer condition can be plantar warts, cardiac hypertrophy, or cancer cachexia.

Compounds of this invention can be administered in combination with other anti-cancer or cytotoxic agents, including alkylating agents, angiogenesis inhibitors, anti-metabolites, DNA cleavers, DNA crosslinkers, DNA intercalators, DNA minor groove binders, enediynes, heat shock protein 90 inhibitors, histone deacetylase inhibitors, microtubule stabilizers, nucleoside (purine or pyrimidine) analogs, nuclear export inhibitors, proteasome inhibitors, topoisomerase (I or II) inhibitors, tyrosine kinase inhibitors. Specific anti-cancer or cytotoxic agents include β-lapachone, ansamitocin P3, auristatin, bicalutamide, bleomycin, bleomycin, bortezomib, busulfan, callistatin A, camptothecin, capecitabine, CC-1065, cisplatin, cryptophycins, daunorubicin, disorazole, docetaxel, doxorubicin, duocarmycin, dynemycin A, epothilones, etoposide, floxuridine, floxuridine, fludarabine, fluoruracil, gefitinib, geldanamycin, 17-allylamino-17-demethoxygeldanamycin (17-AAG), 17-(2-dimethylaminoethyl)amino-17-demethoxygeldanamycin (17-DMAG), gemcitabine, hydroxyurea, imatinib, interferons, interleukins, irinotecan, maytansine, methotrexate, mitomycin C, oxaliplatin, paclitaxel, suberoylanilide hydroxamic acid (SAHA), thiotepa, topotecan, trichostatin A, vinblastine, vincristine, and vindesine.

Preferably, compounds of this invention are provided in a purified and isolated form, for example following column chromatography, high-pressure liquid chromatography, recrystallization, or other purification technique. Where particular stereoisomers of compounds of this invention are denoted, such stereoisomers preferably are substantially free of other stereoisomers.

Compounds of this invention may be used in a pharmaceutical formulation comprising a compound of this invention and an excipient. Excipients that may be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., Remington: The Science and Practice of Pharmacy, 20th Ed. (Lippincott Williams & Wilkins 2003), the disclosure of which is incorporated herein by reference.

The composition may be in any suitable form such as solid, semisolid, or liquid form. In general, the pharmaceutical preparation will contain one or more of the compounds of the invention as an active ingredient in admixture with an organic or inorganic carrier or excipient suitable for external, enteral, or parenteral application. The active ingredient may be compounded, for example, with the usual non-toxic, pharmaceutically acceptable carriers for tablets, pellets, capsules, suppositories, pessaries, solutions, emulsions, suspensions, and any other form suitable for use. The carriers that can be used include water, glucose, lactose, gum acacia, gelatin, mannitol, starch paste, magnesium trisilicate, talc, corn starch, keratin, colloidal silica, potato starch, urea, and other carriers suitable for use in manufacturing preparations, in solid, semisolid, or liquified form. In addition, auxiliary stabilizing, thickening, and coloring agents and perfumes may be used. Preferred modes of administration include intravenously and, in the case of certain indications such a cervical cancer, bladder cancer, or plantar warts, topically.

Where applicable, compounds of this invention may be formulated as microcapsules and nanoparticles. General protocols are described for example, in Bosch et al., U.S. Pat. No. 5,510,118 (1996); De Castro, U.S. Pat. No. 5,534,270 (1996); and Bagchi et al., U.S. Pat. No. 5,662,883 (1997), which are all incorporated herein by reference. By increasing the ratio of surface area to volume, these formulations allow for the oral delivery of compounds that would not otherwise be amenable to oral delivery.

Dosage levels of the compounds of the present invention are of the order from about 0.1 mg to about 100 mg per kilogram of body weight per day, preferably from about 1 mg to about 50 mg per kilogram of body weight per day. More preferably, the dosage levels are from about 5 mg to about 20 mg per kilogram of body weight per day, corresponding to 350 mg to 1400 mg per patient per day, assuming a 70 kg patient. The compounds of the present invention may be administered on an intermittent basis, i.e., at semi-weekly, weekly, semi-monthly, or monthly intervals.

The amount of active ingredient that may be combined with the carrier materials to produce a single dosage form will vary depending upon the host treated and the particular mode of administration. For example, a formulation intended for oral administration to humans may contain carrier material, which may vary from about 5 percent to about 95 percent of the total composition. Dosage unit forms will generally contain from about 5 mg to about 500 mg of active ingredient.

It will be understood, however, that the specific dose level for any particular patient will depend on a variety of factors. These factors include the activity of the specific compound employed; the age, body weight, general health, sex, and diet of the subject; the time and route of administration and the rate of excretion of the drug; whether a drug combination is employed in the treatment; and the severity of the particular disease or condition for which therapy is sought.

Without being bound by theory, we believe that compounds of our invention function by a mechanism analogous to that of LMB to inhibit CRM-1 mediated nuclear export processes in the target cancer cells, thus inducing apoptosis. The 2,3-dehydro-δ-valerolactone moiety in LMB is a Michael reaction acceptor. LMB has been shown to inhibit CRM1 by forming a Michael adduct at this location with cysteine 529 of CRM1 (Kudo et al., Proc. Nat'l Acad. Sci. (USA) 1999, 96 (3), 9112-9117). It has been shown that ratjadone, another member of the leptomycin family, inhibits CRM1 by the same mechanism (Meissner et al., *FEBS Lett.* 2004, 576 (1-2), 27-30). It has also been theorized, on the basis of structural similarity, that the kazusamycins act likewise (Ando et al., *Bioorg. Med. Chem. Lett.* 2006, 16, 3315-3318). The compounds of this invention retain the critical 2,3-dehydro-δ-valerolactone pharmacophore and therefore can be expected to function by the same inhibitory mechanism.

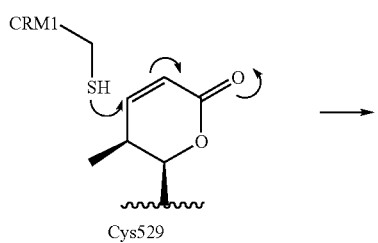

Cys529

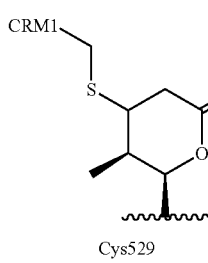

Cys529

228-234; Wang et al., US 2003/0162740 A1 (2003). Thus, the combination of imatinib and an LMB compound of this invention can provide a mechanism for synergistically attacking Bcr-Abl positive cancer cells.

Thus, compounds of this invention can be used to inhibit the nuclear export of proteins such as p53, p73, Bcr-Abl, STAT1, (i) ADAR1, Rev, and actin from the nucleus of a cell, by forming a covalent adduct with CRM1 and interfering with the CRM1 mediated export process for such proteins. In one embodiment, the inhibited protein is p53. In another embodiment, the inhibited protein is Bcr-Abl. While a certain variability is to be expected depending on the cell type and the target protein, generally the inhibitory amount used will be in the range of 0.3 to 740 nM, preferably 0.3 to 20 nM, more preferably 0.3 to 2.0 nM.

The practice of this invention can be further understood by reference to the following examples, which are provided by way of illustration and not of limitation.

Example 1

The following procedure for the preparation of compound 1 is representative:

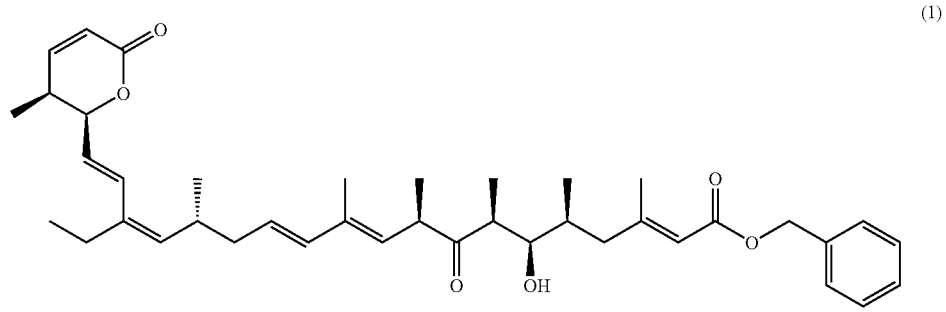

(1)

Many cancer cells have mutations resulting in the loss of function of the apoptosis-inducing, tumor suppressor protein p53. Vousden et al., Nat. Rev. Cancer 2002, 2, 594-504. Examples of such cancers include prostate cancer and human papilloma virus (HPV) associated cervical cancer. It has been shown that LMB causes the accumulation of p53 protein in the nucleus of cervical cancer cells. Lane et al., Proc. Nat'l Acad. Sci. (USA) 2000, 97, 8501-8506. In prostate cancers characterized by defective up-regulation of p53 due to DNA damage, the cell nucleus is deficient in p53. LMB has been shown to trap p53 in the nucleus and induce apoptosis. Hence, prostate cancer cells are highly sensitive to LMB. Peehl et al., Prostate 2003, 54, 258-267.

Against appropriate types of cancers, compounds of this invention can be used synergistically with other anticancer agents, in particular tyrosine kinase inhibitors such as imatinib (whose mesylate is known by the proprietary name Gleevec™). Some cancers such as chronic myelogenous leukemia (CML) are characterized by expression of the fusion protein Bcr-Abl. While normally Bcr-Abl is not imported into the nucleus, the Bcr-Abl/imatinib complex is imported into the nucleus. If LMB is also present, it prevents the export of Bcr-Abl out of the nucleus. Further, nuclear-entrapped Bcr-Abl induces apoptosis, resulting in the death of Bcr-Abl positive cells. See, e.g., Vigneri et al., Nature Medicine 2001, 7, LMB (15.0 mg, 0.028 mmol, 1 eq) was dissolved in dry DMF (300 µL). The reaction was cooled to −50° C. under $N_2$. Benzyl bromide (16.5 µL, 0.14 mmol, 5 eq) was added followed by 1,8-diazabicyclo[5.4.0]undec-7-ene (DBU, 3.8 µL, 0.025 mmol, 0.9 eq). The reaction was allowed to warm to 0° C. over 40 minutes. The reaction was then partitioned between saturated aqueous $NH_4Cl$ and EtOAc. The organic layer was washed with saturated aqueous $NH_4Cl$ (1×), saturated aqueous $NaHCO_3$ (1×), and brine (1×). The organic layer was dried over $Na_2SO_4$, filtered, and concentrated in vacuo to yield a yellow oil. The crude material was applied to a silica flash column (0.5×5 cm) and eluted with a gradient of EtOAc/hexane (0 to 40%). The product eluted in the 30-35% fractions. The fractions were pooled and concentrated in vacuo to provide compound 1 as a clear oil in 37% yield (6.48 mg, 0.010 mmol): $^{13}C$ NMR (100 MHz, $CDCl_3$) δ 12.34, 12.42, 13.05, 13.58, 13.68, 16.05, 18.42, 20.48, 26.55, 32.16, 33.43, 33.52, 40.79, 45.39, 45.60, 46.55, 65.46, 74.33, 81.43, 117.05, 120.06, 122.74, 128.02, 128.15, 128.49, 130.12, 135.16, 135.47, 136.37, 136.43, 136.92, 151.43, 159.03, 164.22, 166.21, 215.20; HRMS calcd for $C_{40}H_{54}O_6Na$: 653.38137; found: 653.38126.

Example 2

Compound 2 was prepared analogously to compound 1, using methyl bromoacetate instead of benzyl bromide.

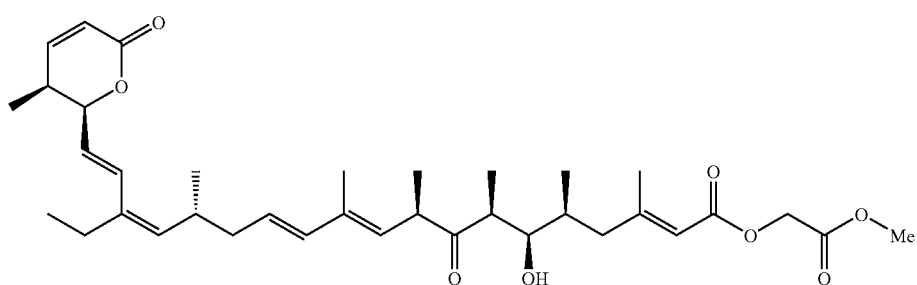

(2)

$^{13}$C NMR (100 MHz, CDCl$_3$) δ 12.35, 12.47, 13.06, 13.58, 13.67, 16.05, 18.57, 20.84, 26.55, 32.18, 33.43, 33.53, 40.79, 45.44, 45.59, 46.55, 52.17, 60.05, 74.29, 81.47116.03, 120.07122.73, 128.06, 128.13, 130.17, 135.15, 135.48, 136.46, 136.93, 151.45, 160.88, 164.24, 165.40, 168.71, 215.18; HRMS calcd for C$_{36}$H$_{52}$O$_8$Na, 635.35492; found 635.35544; yield 64%.

Example 3

Compound 3 was prepared analogously to compound 1, using 8-(bromomethyl)quino line instead of benzyl bromide.

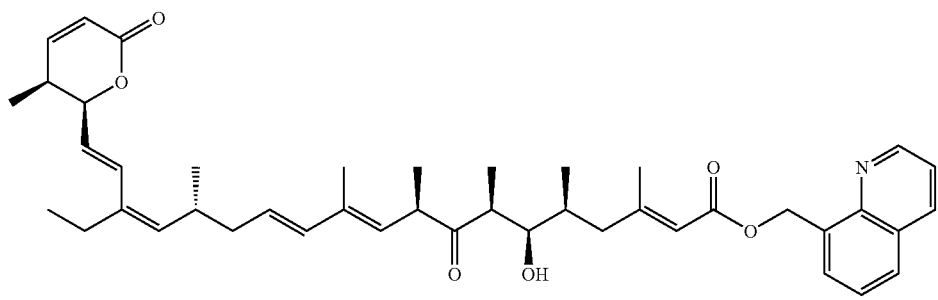

(3)

$^{13}$C NMR (100 MHz, CDCl$_3$) δ 0.97, 12.289, 13.535, 13.713, 16.006, 18.375, 20.801, 26.486, 30.899, 32.109, 33.345, 33.478, 40.739, 45.296, 45.545, 46.397, 61.866, 74.334, 81.434; HRMS calcd for C$_{43}$H$_{56}$NO$_6$, 682.40691; found 682.41022; yield 14%.

Example 4

Comparative

LMB methyl ester (compound 4) was prepared for comparative purposes, using the same procedure as for compound 1, but with 2 M iodomethane in t-butyl methyl ether (4 eq.) and 3 equivalents of DBU.

Those skilled in the art will appreciate that another general approach to ester synthesis may be applicable: in situ preparation of an activated ester (e.g. DCC, acid chloride, Mitsunobu, etc.) via acid nucleophilic attack on the activating agent. The resulting activated ester is then exposed to a nucleophilic alcohol which transesterifies to the more stable desired ester product.

Those skilled in the art will also appreciate that, while the invention has been exemplified hereinabove with specific reference to leptomycin, other esters of this invention can be made from other compounds in the leptomycin family, such as leptomycin A, anguinomycin A or B, or kazusamycin A or B.

Example 5

The biological activity of compounds of this invention was evaluated by measuring their inhibitory effect on the proliferation of various tumor cell lines. Results, including comparative ones for LMB, are tabulated in Table 1. MCF-7, A549, and SKOV-3 are human breast, lung, and ovary cancer cell lines, respectively. NCI/ADR is a multi-drug resistant breast cancer cell line. CCRF-CEM and CCRF-CEM/PTX are human leukemia cell lines, the latter being a paclitaxel-resistant subline.

TABLE 1

| Compound | Tumor Cell Line (IC$_{50}$, nM) | | | | | |
|---|---|---|---|---|---|---|
| | MCF-7 | NCI/ADR | A549 | SKOV-3 | CCRF-CEM | CCRF-CEM/PTX |
| LMB | 0.29 | 1.0 | 0.30 | 1.5 | 0.65 | 0.41 |
| 1 | 3 | 38 | 5.3 | 17 | 2.7 | 4.8 |
| 2 | 0.33 | 5.2 | 2.3 | 5.3 | 1.1 | 1 |
| 3 | 3.7 | 270 | 5.3 | 24 | 5.6 | 14 |
| 4 | 1.9 | 13.1 | 2.4 | 8.2 | 0.55 | 0.63 |

These examples show that the compounds of this invention have cytotoxicities that are generally comparable to that of LMB itself, within an order of magnitude or so.

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

Further, while the present invention has been particularly described in terms of certain preferred embodiments, the invention is not limited to such preferred embodiments. Rather, the scope of the invention is defined by the appended claims.

What is claimed is:

1. A compound having a structure according to formula I

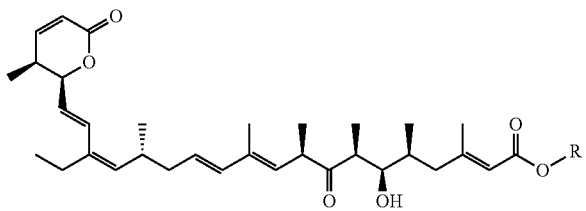

(I)

and the pharmaceutically acceptable thereof,
wherein
R is $CH_2R^1$;
$R^1$ is aryl, heteroaryl, or $C(=O)OR^2$; and
$R^2$ is $C_2$-$C_4$ alkyl, cycloaliphatic, heterocycloaliphatic, aryl, or heteroaryl.
n is 1, 2, 3, or 4.

2. The compound of claim 1, having a structure according to formula 1, 2, or 3:

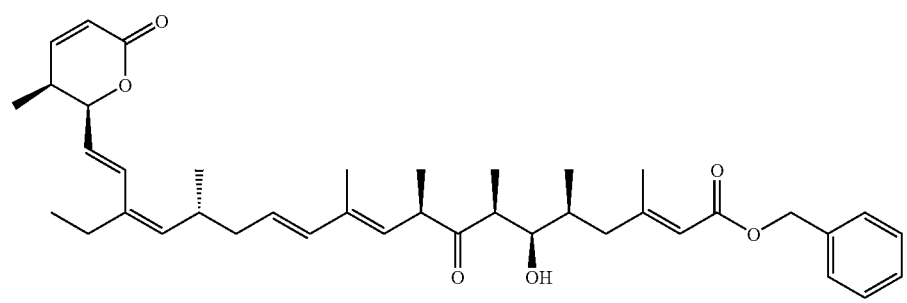

(1)

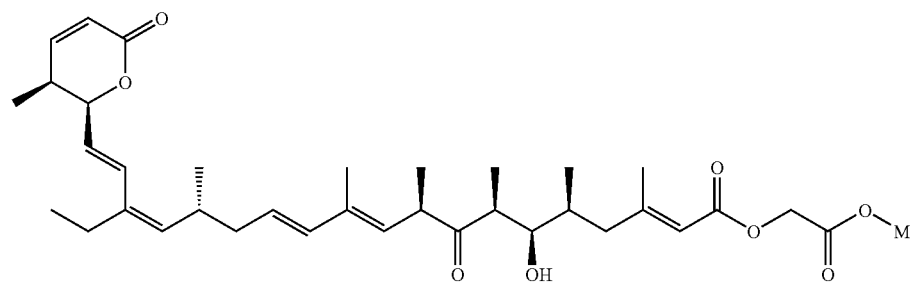

(2)

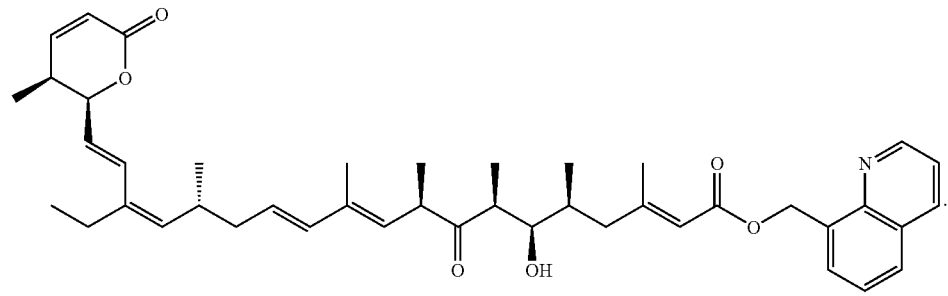

(3)

3. A method of inhibiting the proliferation of tumor cell lines and/or inhibiting the export of a protein from the nucleus of a cell via a CRM1-mediated process, comprising administering to a patient in need of said inhibition a therapeutically effective amount of a compound according to claim 1.

4. The method of claim 3, wherein the patient is a human.

5. A pharmaceutical composition comprising a compound according to claim 1 and an excipient.

* * * * *